United States Patent [19]

Sasao

[11] Patent Number: 5,279,794
[45] Date of Patent: Jan. 18, 1994

[54] PROBE WASHING UNIT AND AUTOMATIC ANALYSIS SYSTEM HAVING PROBE WASHING UNIT

[75] Inventor: Itsuro Sasao, Nishinasuno, Japan

[73] Assignee: Kabushiki Kaisha Toshiba, Kawasaki, Japan

[21] Appl. No.: 969,348

[22] Filed: Oct. 30, 1992

[30] Foreign Application Priority Data

Oct. 31, 1991 [JP] Japan .................. 3-286731

[51] Int. Cl.$^5$ .............................. B01L 3/02
[52] U.S. Cl. .................. 422/100; 422/63; 422/64; 422/99; 73/864.22; 134/140; 134/155; 134/186; 141/89; 141/91; 141/67; 141/130
[58] Field of Search ............. 422/99, 100, 63, 64; 73/864.22; 141/89-91, 67, 130; 134/155, 186, 140, 902

[56] References Cited

U.S. PATENT DOCUMENTS

| | | | |
|---|---|---|---|
| 3,601,162 | 8/1971 | Page | 141/90 |
| 3,911,749 | 10/1975 | Hendry | 73/864.22 |
| 4,076,503 | 2/1978 | Atwood et al. | 422/100 |
| 4,131,426 | 12/1978 | Range | 422/100 X |
| 4,343,766 | 8/1982 | Sisti et al. | 422/100 X |
| 4,456,037 | 6/1984 | Gocho | 422/100 X |
| 4,543,238 | 9/1985 | Mimura et al. | 422/64 X |
| 4,730,631 | 3/1988 | Schwartz | 141/91 X |
| 4,774,055 | 9/1988 | Wakatake et al. | 422/100 X |
| 4,948,563 | 8/1990 | Kanewske, III | 422/99 |
| 4,989,623 | 2/1991 | Hoffman et al. | 141/90 X |

Primary Examiner—James C. Housel
Assistant Examiner—Maureen M. Wallenhorst
Attorney, Agent, or Firm—Oblon, Spivak, McClelland, Maier & Neustadt

[57] ABSTRACT

A washing apparatus for washing a probe which is transferred substantially horizontally in a plane during a washing process includes a washing body having a wall structure defining an inner hollow portion, a feed water unit provided for the wall structure of the washing body for feeding water in the inner hollow portion, slits formed in the wall structure of the washing body so as to communicate with the inner hollow portion of the washing body, and at least a first waterway channel having one end connected to a bottom portion of at least one of the slits and a second, free end, wherein the waterway channel is disposed on a level substantially corresponding to a transfer route of a tip of the probe and has a shape so as to substantially correspond with the transfer route of the probe. The waterway channel is formed so that the tip of the probe is most deeply dipped at a portion near the one end of the waterway channel connected to the slit of the washing body and then is separated from the waterway channel at a portion near the free end of the waterway during the horizontal transfer of the probe. The probe washing apparatus can be utilized particularly for a random access type automatic analysis system for washing the probe after suction of a sample or reagent into the probe before reaching a reaction tube.

17 Claims, 5 Drawing Sheets

PROBE WASHING UNIT AND AUTOMATIC ANALYSIS SYSTEM HAVING PROBE WASHING UNIT

BACKGROUND OF THE INVENTION

1. Field of the Invention

The present invention relates to a probe washing unit and an automatic analysis system, particularly of a random access type, provided with the probe washing unit.

2. Discussion of the Background

In a usual random access type automatic analysis system, when a sample in a sample container such as sample tube accommodated in a sampler, for example, is sucked and discharged into a reaction tube by utilizing a slender dispensation, i.e. sample probe, the sample usually in a liquid state adheres to the outer surface of the tip end of the probe at the time of suction and may be dropped into the reaction tube together with the sample inside the probe to be weighed at the time of discharge, thus deteriorating the sample dispensing precision as well as the measurement precision.

In order to obviate such defects, the sample adhering to the outer surface of the tip portion of the probe is removed by wiping the same or dipping the same into a clean liquid such as pure water.

In the wiping method, the tip portion of the probe is held by a wiper having a liquid absorbing property and moving the probe upward. On the other hand, in the dipping method, the dispensation probe is dropped in a washing unit during the analyzing process after sucking the sample and the sample adhering to the outer surface of the probe tip is diffused by washing water in the washing unit and then wiped.

Furthermore, when dispensing a sample and a reagent in the automatic analysis system, the inside and outside of the dispensation probe are washed in the washing unit after the sample and the reagent are dispensed. However, since a drop of the washing water is typically attached to the probe after the washing, the drop is wiped off and likely removed as in the case of the above mentioned wiping method.

However, in the wiping method, since various samples are treated by the wiper one after another, these become stained and cause contamination of the samples. In particular, the recent type of an automatic analysis system operates with a high degree of sensitivity, and hence, that with the normal value being several tens, for example, in AFP (Anti-Feto-Protain) the measurement becoming several thousands according to the condition of a patient, if the sample is sucked from the patient, thus bringing about a problem of a minute contamination of the samples.

On the other hand, in the dipping method, even if a high-speed operation of the automatic analysis system is realized, too much time is required for the vertical motion of the dispensation probe in the washing unit during the horizontal transfer of the dispensation probe, and, hence, there still remains a disadvantage of not coping with the high-speed operation. Now, therefore, in order to cope with the high-speed operation, a proposal has been made such that the dispensation probe the washed with flushing water with its tip, i.e. front, portion kept at a transfer height at a flushing position. However, in this method, since the flushing water is applied to the dispensation probe for washing the same, the probe will be transferred to the next vessel position with a drop of water being attached to the probe tip after the stopping of the water feed. As a result, the drop of water having attached to the probe tip is scattered or the drop is mixed into the sample or reagent, thus causing a disadvantage such as providing inferior data precision or degraded and denatured reagent and sample.

SUMMARY OF THE INVENTION

An object of the present invention is to substantially eliminate defects or disadvantages encountered in the prior art described above and to provide a washing unit capable of precisely wiping away flushing water, sample or reagent having become attached to a dispensation probe which is transferred substantially horizontally in a plane and which is capable of cutting the time for water flushing or washing process more sharply than that in the prior art.

Another object of the present invention is to provide an automatic analysis system provided with a washing unit of the character described above.

These and other objects can be achieved according to the present invention by providing, in one aspect, a washing apparatus for washing a probe which is transferred substantially horizontally in a plane during a washing process, comprising:

a washing body having a wall structure defining an inner hollow portion;

a water feeding means provided for the wall structure of the washing body for feeding water in the inner hollow portion;

a slit formed in the wall structure of the washing body so as to communicate with the inner hollow portion of the washing body; and channel means constituting at least one waterway having one end connected to a bottom portion of the slit and another free end, wherein channel means is disposed on a level slightly lower than a transfer route of a tip of the probe and has a shape substantially along the transfer route of the probe and wherein the waterway is formed so that the tip of the probe is dipped deepest at a portion near the one end of the waterway connected to the slit of the washing body and then apart from the waterway at a portion near another free end of the waterway during the horizontal transfer of the probe.

The waterway has a curved shape along the transfer route of the probe.

The waterway has a downward inclination from the one end connected to the slit of the washing body towards a free end of the waterway.

In a modification, the waterway is disposed horizontally at the same level and is provided with a bottom wall and side walls, the side walls each having a height which is gradually reduced from one end thereof connected to the slit of the washing body towards a free end thereof so that feed water through the water feeding means and the inner hollow portion of the washing body overflows over the side walls before reaching the free end of each of the side walls.

The channel means comprises one waterway and the slit includes a first slit to which one waterway is connected and a second slit formed substantially opposingly to the first slit, the first and second slits having substantially the same depth.

In a further modification, the channel means comprises first and second waterways and the slit includes a first slit and a second slit formed substantially opposite to the first slit, the first and second slits having depths substantially equal to each other and the first and second waterways being connected to the first and second slits, respectively.

In another aspect of the present invention, there are provided an automatic analysis system in which probes to be washed is transferred substantially horizontally in a plane during a probe washing process, comprising:

a sample unit in which a number of sample vessels are accommodated;

a reagent storage unit in which a number of reagent vessels are accommodated;

a reaction unit in which a number of reaction tubes are accommodated;

a first swing arm member provided with a probe and disposed in association with the sample unit to be swingable between the sample unit and the reaction unit;

a second swing arm member provided with a prode and disposed in association with the reagent storage unit so as to be swingable between the reagent storage unit and said reaction unit;

a third swing arm member provided with a probe and disposed in association with the reaction unit; and first, second and third probe washing apparatus disposed in association with said first, second and third swing arm members, respectively, for washing the probes, wherein each of the probe washing apparatus is disposed along a transfer route of a probe so that the probe to be washed is first dipped deepest and then gradually reduced in dipping length during the probe washing process.

In this aspect, the probe washing apparatus may have substantially the same structure as that described with reference to the above first aspect of the present invention.

According to the probe washing apparatus and the automatic analysis system provided with the probe washing appratus of the charaters described above, the probe after sucking a sample, for example, from the sample vessel is moved substantially horizontally in a plane and the probe can be washed during its washing process along the transfer route. The tip of the probe, during this washing process, is first dipped deepest and then is gradually reduced in dipping depth towards the reaction tube, for example, thus surely wiping the liquid adhering to the outer surface of the probe.

The further nature and features of the present invention will be described in greater detail hereafter with reference to the accompanying drawings.

DESCRIPTION OF THE PREFERRED EMBODIMENTS

Figure 1:
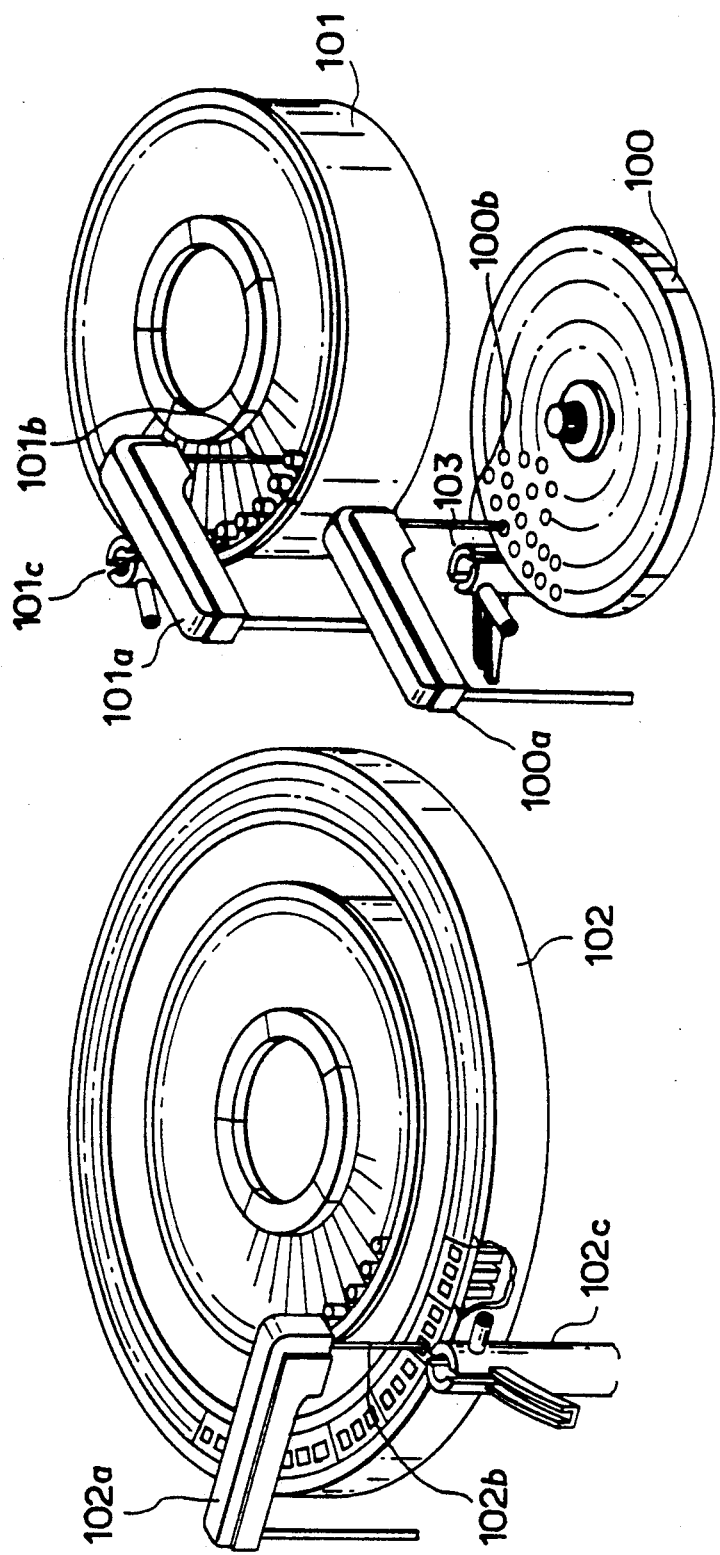
FIG. 1 is a perspective view showing a general arrangement of a random access type automatic analysis system according to the present invention.

FIG. 1 is a perspective view showing an arrangement units or elements of a random access type automatic analysis system. In FIG. 1, the automatic analysis system generally comprises a sampler 100 in which a number of sample tubes or the like are accommodated in each of which a sample is accommodated, a reagent storage unit 101 in which a number of reagent tubes or the like are accommodated in each of which a reagent is accommodated and a reaction unit 102 within which a number of reaction tubes such as tubes or the like and a number of reagent tubes or the like are also accommodated. These units 100, 101 and 102 are generally constructed so as to have a disc shape and are rotatable. A sample swing arm 100a is located near and in association with the sampler 100 and a dispensation probe, i.e. a sample probe 100b is attached to the sample swing arm 100a to sample a sample in the sample tube. A reagent dispensing swing arm 101a is located near and in association with the reagent storage unit 101 and a dispensing probe 101b is attached to the reagent dispensing swing arm 101a to suck out the reagent in the reagent tube. The sampling arm 100a and the reagent dispensing arm 101a are vertically movable and horizontally rotatable so that the sample and reagent sucked can be transferred into the reaction tubes located in the reaction unit 102. A reagent dispensing swing arm 102a is also located near and in association with the reaction unit 102. These units 100, 101 and 102 are all arranged so as to be rotatable on a table unit, not shown in FIG. 1, in one system and each of these units shown in FIG. 1 include portion shown with image lines, which are substantially the same as those shown with solid lines.

In the random access type automatic analysis system of the type described above, an agitation unit, an optical measurement unit, both not shown, and a washing unit are also disposed. Three washing units 103, 101c and 102c are disposed in the system shown in FIG. 1 in association with the sample arm 100a and the reagent dispensing arms 101a and 102a, and only the washing unit 103 is fully shown in FIG. 1 in association with the sample arm 100a because these washing units have substantially the same structure.

The washing unit 103 acts to wash the sample probe 100b during the transfer of the sample probe 100b from the sample position to the reaction unit, i.e. reaction tubes by flushing water to the sample probe 100b, and this transfer of the sample probe 100b is made substantially horizontally in a plane.

Figure 2:
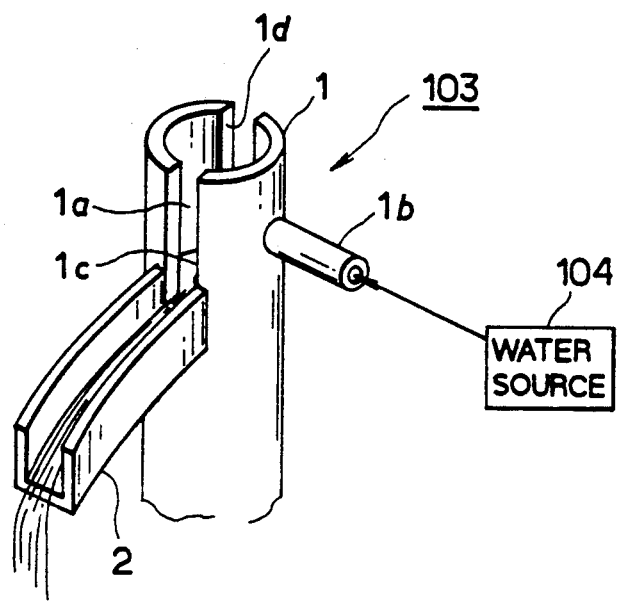
FIG. 2 is a perspective view of one embodiment of a probe washing apparatus according to the present invention, which may be applicable to the system shown in FIG. 1.

FIG. 2 shows an illustrated perspective view of the washing unit 103, and in FIG. 2, the washing unit 103 is composed of a cylindrical body 1 provided with slits 1a and 1d formed as cutouts in the wall of the cylindrical body 1, a feed water port 1b also provided for the wall of the body 1 and a channel-shaped waterway 2 having one end connected to the body 1 at a portion of the slit 1a. The waterway 2 is formed as a channel member having a bottom wall and two side walls. In this embodiment, the slits 1a and 1d have bottom portions positioned on a level slightly lower than the front end of the tip of the probe during the horizontal transfer thereof.

The waterway 2 is provided along a transfer route of the sample probe 5, corresponding to the probe 100b in FIG. 1, connecting a span between the washing unit 103 and the reaction unit 102, i.e. reaction tubes 3, and the span between the washing unit 103 and a sampler 100, i.e. sample tube 4, continuously, and the waterway 2 is disposed substantially level with or slightly lower than the transfer height of the tip of the sample probe 5 after sucking out of the sample from the sample tube 4 has occurred. As described above the transfer route is generally arcuate, which may be determined by the size of the sampler, the reaction unit and the sample arm as well as the span between the reaction unit and the sampler. Accordingly, the waterway 2 may be also formed so as to provide a curved waterway path along the arcuate transfer route of the sample probe 5.

Figure 3:
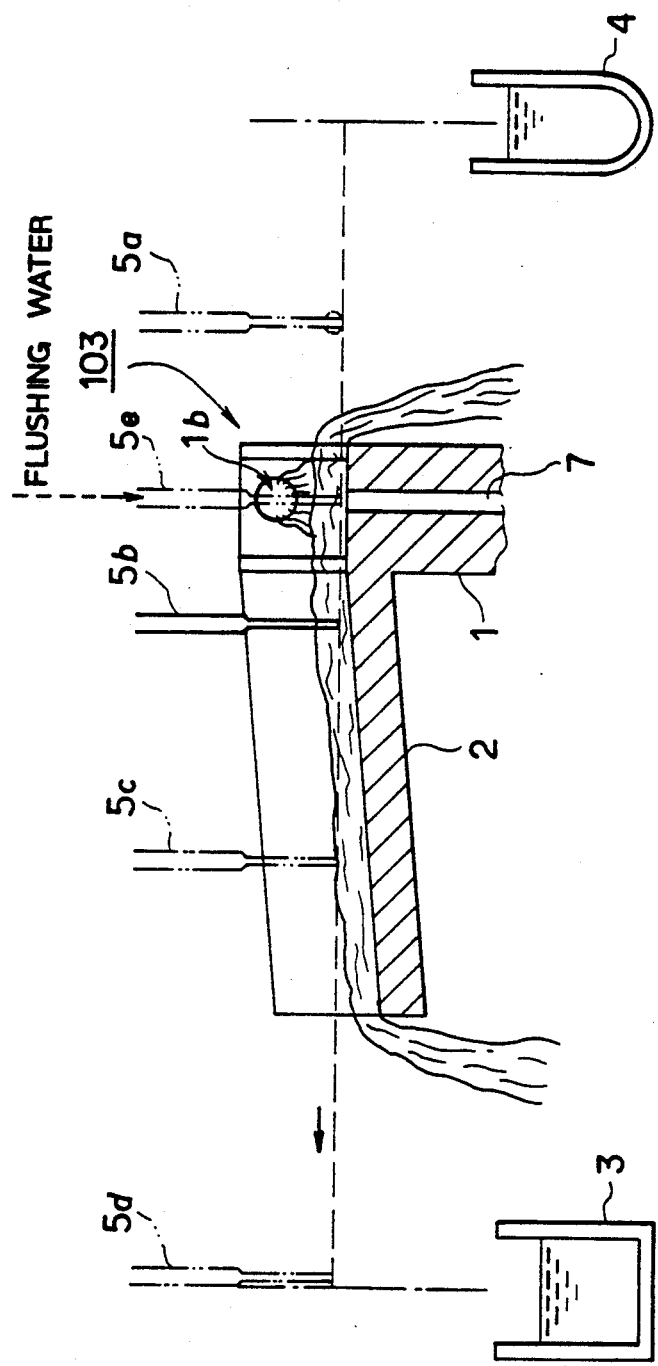
FIG. 3 is a side view, partially in section, of the washing unit of FIG. 2 for explaining the probe washing process.

The cylindrical body 1 of the washing unit 103 has an inner hollow portion formed at the upper end portion thereof and the hollow portion is of a vessel shape having an upper open end, a bottom portion 1c and the slits 1a and 1d. The bottom portion 1c is located at a level substantially flush with the connection of the waterway 2, but the bottom 1c is provided with a fine hole 7 described hereinafter. The water fed from a water source 104 through the feed water port 1b is once supplied in the vessel shaped hollow portion of the cylindrical body 1 and then flows towards the waterway 2. This waterway 2 has an downward inclination as shown in FIG. 2 or 3, thus causing the water to flow downwardly.

As described above and as shown in FIG. 3, the waterway 2 forms a gradient one with its bottom gradually descending from a position of connection with cylindrical body of the washing unit 103. The transfer of the sample probe 5 is shown in FIG. 3 in order. Namely, the sample probe 5 after sampling the sample from the sample tube 4 is moved towards the body 1 of the washing unit 103 substantially horizontally in a plane through the operation of the sample arm 100a as shown by a position of reference numeral 5a, and when the sample probe 5 arrives at the position of the washing body 1 of the unit 103 through the slit 1d, the probe is most deeply dipped in the waterway 2 at the position indicated by reference numeral 5b. The probe 5 is then transferred substantially horizontally along the shape of the waterway 2 towards the reaction tube 3 while the dipped length of the tip thereof becoming gradually reduced, as shown by reference numeral 5c, and reaches a position above the reaction tube 3 as shown by reference numeral 5d. Then, since the probe tip moves away from the washing water in the waterway 2 before arriving at the position above the reaction tube 3, any liquid adhering to the outer surface of probe tip can be wiped off.

When the sample probe 5 has arrived at the reaction tube 3, the sample contained in the probe 5 is fed into the reaction tube 3, and thereafter, the sample probe 5 moves to a position above the washing body 1 of the washing unit 103 substantially horizontally in a plane as shown by reference numeral 5e at which the probe tip is positioned inside the inner space of the body 1. At this position, a washing liquid is flushed violently inside the sample probe 5 to wip off any of the sample which may adhere to the inner wall of the probe tip. This flushed washing water is drained through the hole 7 formed to the bottom of the inner hollow portion of the washing body 1. The hole 7 has a very small diameter so that only the violently flushed washing water is drained and the flushing water fed through the feed water port 1b is not drained into hole 7 due to the surface tension thereof. In this connection, it is to be noted that it is preferred for the hole 7 to have a diameter about twice or more than that of the tip end of the sample probe 5. In an actual example, the tip of the sample probe has an inner diameter of about 0.6 mm and a wall thickness of about 0.2 to 0.5 mm, the tip of the reagent tube has an inner diameter of about 1.0 to 1.6 mm and a wall thickness of about 0.2 to 0.5 mm.

In the foregoing discussion, although the waterway 2 is described as having a curved structure, it may be formed as a substantially linear structure in accordance with the transfer route of the sample probe 5 and the waterway 2 may be formed like a trough having a round bottom.

Figure 4:
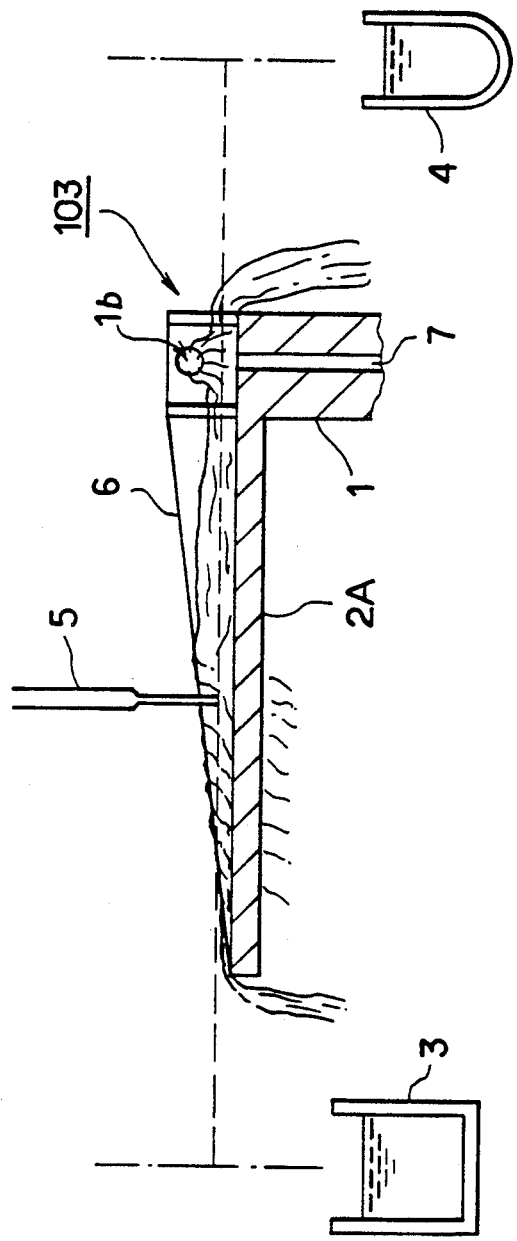
FIG. 4 is a view similar to that of FIG. 3 showing another embodiment of the probe washing apparatus according to the present invention.

FIG. 4 shows a modification of the embodiment of FIG. 3, in which the waterway 2 is disposed horizontally at a level substantially according to the transfer route of the tip of the sample probe 5.

Referring to FIG. 4, a waterway 2A has side walls each having a height which is gradually reduced in the direction towards the reaction tube 3, and in the illustration of FIG. 4, the end portions of the side walls 6 of the waterway 2A connected to the washing body 1 of the washing unit 103 have heights corresponding to the entire vertical length of the slit 1a and then the height of the side walls 6 is gradually reduced. According the water fed through the feed water port 1b flows along the waterway 2A towards the reaction tube 3 due to the feeding force of the water, but the water overflows over the side walls of the waterway 2A in passing towards the reaction tube 3 because the walls are each gradually reduced in heights. Accordingly, the sample probe 5, which is transferred horizontally in a plane along and parallel to the waterway 2A, is first most deeply dipped at the portion of the waterway 2A near the connected end thereof, and the dipped depth of the tip of the probe 5 is gradually reduced towards the reaction tube 3 and then apart from the water surface before arriving above the reaction tube 3, thus wiping the liquid adhering to the outer surface of the tip portion of the probe 5. Other structures and operations in this embodiment are substantially the same as those in the embodiment shown in FIG. 2 or 3.

Figure 5:
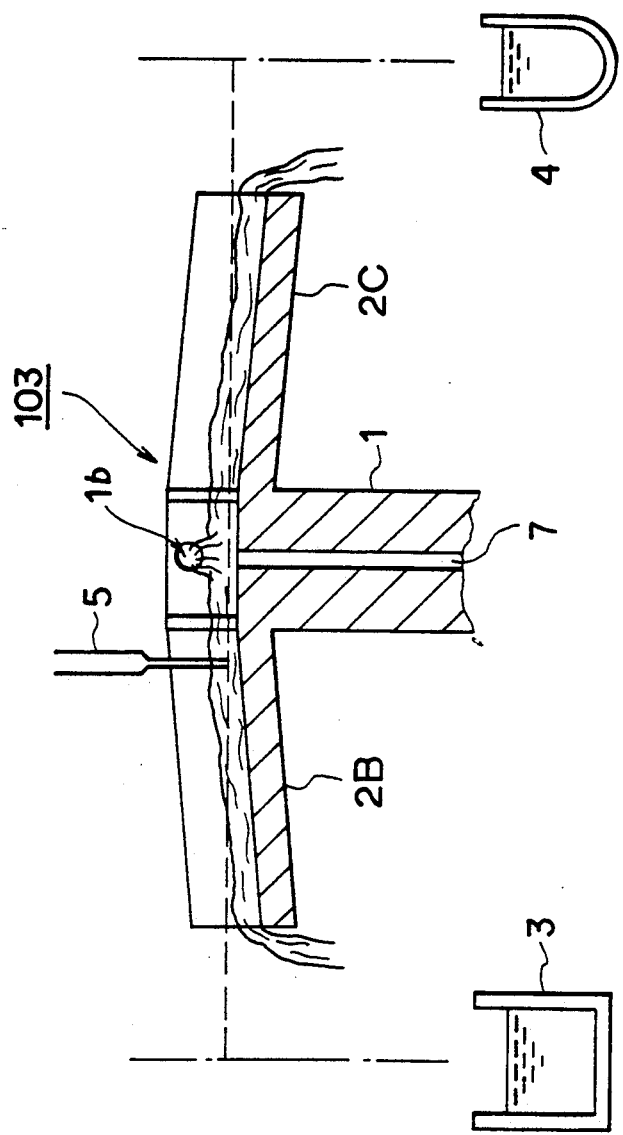
FIG. 5 is a view also similar to that of FIG. 3 or 4 but showing a further embodiment according to the present invention.

FIG. 5 shows a further embodiment of the present invention and, in this embodiment, two waterways 2B and 2C are provided, and the waterway 2B substantially corresponds to the waterway 2 in FIG. 3 while the waterway 2C has a structure substantially the same as the waterway 2B. The waterway 2C has one end connected to the bottom portion of the slit 1d so as to communicate therewith and has an inclination gradually lowered towards the sample tube 4. The waterway 2C may also have an arcuate shape along the transfer route of the probe 5 between the washing unit 103 and the sampler 100, FIG. 1.

In this embodiment, the sample probe 5 after the sample of the liquid in the sample tube 4 is transferred towards the washing unit 103 along the waterway 2C while the tip end of the probe 5 is dipped gradually deeply towards the washing unit 103. After reaching the washing unit 103, the movement of the sample probe 5 is substantially the same as that described with reference to the first embodiment of FIG. 3. According to this embodiment, the probe 5 can be further wiped and cleaned.

It is to be noted that the structure of FIG. 4 may be of course applied to the embodiment of FIG. 5.

According to all the embodiments described above, the tip end of the probe can be dipped in the washing water first deepest and then gradually reduced in of its dipped length even during substantially horizontally transfer of the sample probe without effecting any vertical movement or transfer of the sample probe during the washing process, thus eliminating the washing time as well as performing the improved washing operation.

In the foregoing embodiments, the washing unit 103 disposed between the sampler 100 and the reaction unit 102 is only described with reference to the sample arm 100a being provided with the sample probe 100b, with reference to FIG. 1, but these embodiments are of course applicable to the washing units disposed in association with the dispensing arms 101a and 102a of the reagent storage unit 101 and the reaction unit 102.

Furthermore, it is to be noted that the present invention can be applied to the washing unit for any other apparatus or system in which a liquid dispensation probe is transferred substantially horizontally in a plane during the washing process, in which it is only neccessary that the dispensation probe to be washed is transferred in a plane having an inclination with respect to the flow of the washing water so that the tip of the probe is dipped first deepest and then reduced in the dipped length gradually during the washing process thereof.

What is claimed is:

1. A washing apparatus for washing a probe which is transferred along a route substantially horizontally in a plane during a washing process, which comprises, in combination:
   a probe;
   means for moving said probe in a plane substantially horizontally;
   a washing body having a wall structure defining an inner hollow portion;
   water feeding means connected with the wall structure of the washing body for feeding water into the inner hollow portion, the wall structure having at least one slit formed therein so as to communicate with the inner hollow portion of the washing body; and
   a channel forming at least one waterway having one end connected to a bottom portion of the at least one slit and a free end, wherein said channel is disposed at a level substantially corresponding to a horizontal transfer route of a tip of the probe such that said probe passes along said channel during said transfer route, and wherein said at least one waterway is formed so that the tip of the probe is most deeply dipped into water in said channel from said water feeding means at a portion near the one end of said at least one waterway connected to the at least one slit of the washing body and then is withdrawn from water in said at least one waterway at a portion near the free end of said at least one waterway during horizontal transfer of the probe without having to move the probe vertically up or down.

2. A probe washing apparatus according to claim 1, wherein said at least one waterway has a substantially linear shape in the direction of the transfer route of the probe.

3. A probe washing apparatus according to claim 1, wherein said at least one waterway has a curved shape in the direction of the transfer route of the probe.

4. A probe washing apparatus according to claim 1, wherein said at least one waterway has a downward inclination from the one end of said at least one waterway connected to the at least one slit of the washing body towards the free end of said at least one waterway.

5. A probe washing apparatus according to claim 1, wherein said at least one waterway is disposed horizontally so as to be at a substantially constant level and has a bottom wall and a pair of side walls, said side walls each having a height which is gradually reduced from a first end thereof which is connected to the at least one slit of the washing body towards a second free end thereof so that a flow of water fed through the water feeding means and the inner hollow portion of the washing body overflows over the side walls as the flow of water reaches the second, free end of the side walls.

6. A probe washing apparatus according to claim 1, wherein said inner hollow portion is defined by a bottom wall disposed on a level substantially equal to a bottom of said at least one slit and said bottom wall of the inner hollow portion has a hole having a diameter larger than an inner diameter of the tip of the probe.

7. A probe washing apparatus according to claim 1, wherein said at least one waterway comprises a single waterway and said at least one slit includes a first slit to which the at least one single waterway is connected and a second slit formed substantially opposite to the first slit in the wall structure of the washing body, said first and second slits having substantially the same depth.

8. A probe washing apparatus according to claim 1, wherein said at least one waterway comprises first and second waterways and said at least one slit includes a first slit and a second slit located opposite the first slit, said first and second slits in the wall structure of the washing body having depths substantially equal to each other and said first and second waterways being connected to the first and second slits, respectively.

9. An automatic analysis system in which probes to be washed are transferred along a transfer route substantially horizontally in a plane during a probe washing process, comprising, in combination:
   a first, second and third probe;
   means for moving said first, second and third probes substantially horizontally in a plane;
   a sample unit in which a plurality of sample vessels are accommodated;
   a reagent storage unit in which a plurality of reagent tubes are accommodated;
   a reaction unit in which a plurality of reaction tubes are accommodated, wherein said sample unit, said reagent storage unit and said reaction unit are mounted on a table;
   a first swing arm member provided with said first probe and disposed in association with said sample unit so as to be swingable between the sample unit and the reaction unit;
   a second swing arm member provided with said second probe and disposed in association with said reagent storage unit so as to be swingable between the reagent storage unit and said reaction unit;
   a third swing arm member provided with said third probe and disposed in association with said reaction unit; and
   first, second and third probe washing devices disposed in association with said first, second and third swing arm members, respectively, for washing the first, second and third probes as the probes move horizontally along various transfer routes between the sample unit, reagent storage unit and reaction unit, at least one channel in each of said first, second and third probe washing devices; and water feeding means connected to each of said channels wherein each of said first, second and third probe washing devices is disposed along a transfer route of said first, second and third probes, respectively, so that the first, second and third probes are washed by being first most deeply dipped into water located in each of said channels from said water feeding means and then being dipped at a gradually reduced depth as the movement of the first, second and third probes progresses along said respective transfer routes.

10. An automatic analysis system according to claim 9, wherein each of said probe washing devices comprise:

a washing body having a wall structure defining an inner hollow portion wherein said water feeding means is connected with the wall structure of the washing body for feeding water into the inner hollow portion, the wall structure having first and second opposed slits located in the wall structure; and each of said channels comprises at least one waterway having a first end thereof connected to a bottom portion of said first slit, wherein said at least one channel is disposed at a level substantially corresponding to a horizontal transfer route of a tip of each of said first, second and third probes such that said probes pass along said at least one channel during said transfer route, and wherein said at least one waterway is formed so that the tip of each of said probes is, respectively, most deeply dipped into water in said at least one channel from said water feeding means at a portion near the one end of said at least one waterway connected to the first slit of the washing body and then is withdrawn from said at least one waterway at a portion near a free end of said at least one waterway during the horizontal transfer of each of said probes without having to move said probes vertically up or down.

11. An automatic analysis system according to claim 10, wherein said at least one waterway of each of said probe washing devices has a linear shape along the transfer route of the probes.

12. An automatic analysis system according to claim 10, wherein said at least one waterway of each of said probe washing devices has a curved shape along the transfer route of the probes.

13. An automatic analysis system according to claim 10, wherein said at least one waterway of each of said probe washing devices is downwardly inclined from the end connected to the first slit of the washing body towards a free end of said at least one waterway.

14. An automatic analysis system according to claim 10, wherein said at least one waterway of each of said probe washing devices is disposed horizontally so as to be at a substantially constant level and has a bottom wall and a pair of side walls, said side walls each having a height which is gradually reduced from the end of said at least one waterway connected to the first slit of the washing body towards a free end of said at least one waterway so that a flow of water fed through the water feeding means and the inner hollow portion of the washing body overflows over the side walls as the flow of water reaches the free end of said at least one waterway.

15. An automatic analysis system according to claim 10, wherein said inner hollow portion of the washing body in each of said probe washing devices is defined by a bottom wall disposed on a level equal to the level of a bottom of the first slit and said bottom wall of the inner hollow portion has a hole having a diameter larger than an inner diameter of the tip of one of said first, second and third probes.

16. An automatic analysis system according to claim 10, wherein said at least one waterway of each probe washing device comprises a single waterway connected to said first slit in the wall structure of said washing body.

17. An automatic analysis system according to claim 10, wherein said at least one waterway of each probe washing device comprises first and second waterways, said first and second slits in the wall structure of said washing body have equal depths and said first and second waterways are connected to the first and second slits, respectively.

* * * * *